United States Patent
Lowry et al.

[19]

[11] Patent Number: 6,098,448

[45] Date of Patent: Aug. 8, 2000

[54] IN SITU MEASUREMENT APPARATUS AND METHOD OF MEASURING SOIL PERMEABILITY AND FLUID FLOW

[76] Inventors: William E. Lowry, 17 Valencia Loop, Sante Fe, N. Mex. 87505; Neva Gray Mason, 815 Allendale St., Santa Fe, N. Mex. 87501; Daniel Merewether, 62A Entrada La Cienga, Santa Fe, N. Mex. 87501

[21] Appl. No.: 09/061,078

[22] Filed: Apr. 15, 1998

[51] Int. Cl.$^7$ .................................................. G01N 15/08

[52] U.S. Cl. ............................ 73/38; 73/152.41; 175/21; 175/50

[58] Field of Search .................................. 73/38, 152.41, 73/864.74; 175/21, 50

[56] References Cited

U.S. PATENT DOCUMENTS

| | | | |
|---|---|---|---|
| 2,210,546 | 8/1940 | Hassler | 73/864.74 |
| 2,979,134 | 4/1961 | Reed et al. | 73/152.41 X |
| 3,181,608 | 5/1965 | Palmer | 73/152.41 X |
| 3,871,218 | 3/1975 | Louis | 73/152.41 |
| 4,742,459 | 5/1988 | Lasseter . | |
| 4,936,139 | 6/1990 | Zimmerman et al. . | |
| 5,465,628 | 11/1995 | Timmons . | |
| 5,548,991 | 8/1996 | Ritson | 73/38 |
| 5,698,799 | 12/1997 | Lee, Jr. et al. | 73/864.74 X |
| 5,744,730 | 4/1998 | Ballard et al. . | |

*Primary Examiner*—Daniel S. Larkin
*Attorney, Agent, or Firm*—Kevin Lynn Wildenstein, Esq.

[57] ABSTRACT

An apparatus and method for discrete soil gas and saturated liquid permeability measurements with direct push emplacement systems (such as a cone penetrometer rod). A modified direct push emplacement system having at least one injection port and at least two measurement ports is first engaged to penetrate the soil to a predetermined depth. Gas or liquid is then injected into the soil at a predetermined location on the penetrometer rod. Next, a pressure response is recorded from each measurement port, which is at a known distance from the injection port (on the same penetrometer rod). This differential pressure response data allows calculation of the soil permeability directly by using a one-dimensional, spherical, steady state, porous flow model to measure the effective permeability of the soil, without substantial disturbance of the surrounding soil. The present invention minimizes false indications of reduced permeability as a result of soil compaction during the penetrometer emplacement.

28 Claims, 9 Drawing Sheets

IN SITU MEASUREMENT APPARATUS AND METHOD OF MEASURING SOIL PERMEABILITY AND FLUID FLOW

FIELD OF THE INVENTION

The present invention relates to a soil characterization apparatus and method for using the same, and more particularly, to a characterization apparatus, and a method to employ such apparatus, which is adapted for use with cone penetrometer rods and other direct push emplacement technologies, for subsurface contaminant plume and landfill measurement testing.

BACKGROUND OF THE INVENTION

The permeability of soil is defined as the soil's conductivity to fluid flow. The permeability of soil to fluid flow depends upon the magnitude of soil gas and groundwater flow when subjected to particular natural and/or unnatural pressure gradients. Pressure gradients exist due to natural effects such as hydraulic gradients (in the case of groundwater) and barometrically imposed gradients (in the case of soil gas). Unnatural (forced) gradients can be imposed by soil vapor extraction, air sparging, active venting, pump and treat, and other remediation processes requiring the movement of fluids through the soil.

The design of any of these processes requires a knowledge of the flow characteristics of the soil to be remediated. The soil's permeability is the largest variable, which can vary by orders of magnitude in any given hydrological and/or geological environment. Therefore, knowledge of soil gas permeability is required to design soil vapor extraction systems and understand, in general, the movement of gas in the soil. Similarly, knowledge of saturated hydraulic conductivity (or, the soil's permeability to liquid flow) is required to predict movement of groundwater in saturated soils.

Soil permeability has historically been measured either in laboratories on a very small scale or in the field on a very large scale. Laboratory measurements rarely agree with data collected in the field due to the difficulty of obtaining truly undisturbed soil samples. Further, laboratory test results are usually at least an order of magnitude lower than actual field results.

Because of the high cost and time constraints of obtaining field measurements, it is oftentimes beneficial to first obtain soil permeability measurements in a laboratory setting. The flow of fluid and the travel of contaminant plumes in subsurface soils are capable of being mathematically modeled if the soil's permeability is known. Frequently, however, it is difficult to readily determine the accuracy of the soil's permeability for several reasons. For example, soil is heterogeneous in varying degrees, usually depending upon the type of soil in the surrounding environment, the depth of the soil and the physical scale of interest. Additionally, it is known that soil permeability can vary between two to three orders of magnitude at most soil remediation sites. Consequently, the ability to obtain quality predictive modeling results in the laboratory, whether to estimate soil gas travel or to design alternative remediation systems, is heavily dependant upon the accuracy of the predicted soil permeability and the surrounding environment.

In the field, soil gas permeability measurements are obtained either through total borehole flow or isolated packer (also referred to as a "straddle packer") measurement techniques. Total borehole flow measurements are obtained from open or screened boreholes, where gas or liquid is injected into or extracted from the borehole well. In particular, permeability measurements (gas or liquid) are typically obtained from boreholes using a cylindrical flow model and geometry. Long screened or uncased sections of the borehole are subjected to unnatural (e.g., forced) pressure gradients and the resultant flow into or out of the well is subsequently measured in order to obtain the soil permeability. For one-dimensional radial symmetric (cylindrical) flow geometries such as these, the test region is relatively long and a radius of influence is either measured (or can be predicted) to determine the surrounding soil's permeability. The inherent weakness with this approach, however, is that it results in providing only an average permeability over the test region, and cannot delineate stratigraphic features within any particular test region or depth.

A disadvantage to the current method of obtaining permeability measurements in the field is that it is impossible to translate unmodified open borehole measurement techniques to penetrometer measurement because of size limitations and the penetrometer's compaction of the soil.

Various direct push measurement techniques exist, with perhaps the use of penetrometer rods (or, "penetrometers") being the most common. The direct push technologies using penetration rods include an elongated rod which is pushed into the ground to penetrate the ground and subsurface depths. Generally, each penetrometer rod is a continuously cylindrical steel tube having a hollow interior channel. At one end of some penetrometer rods (e.g., the end which is embedded in the ground) is placed a cone-shaped tip (seen generally in FIG. 3). These types of penetrometers are referred to as "cone penetrometers." If desired, the penetrometer rod can travel deeply into the subsurface by the assistance of a hydraulic ram or other conventional means.

Use of a penetrometer rod to obtain permeability data is inherently less intrusive than drilling boreholes. Penetrometers provide vastly more data in the same amount of time as do drilled holes, at a much lower cost and risk to the operators of penetrometer. Penetrometers, and other direct push techniques (such as the ResonantSonic system) are rapidly advancing as hole formation and soil characterization tools because they are capable of emplacement in difficult media. Therefore, conducting permeability measurements with direct push techniques, instead of in drilled boreholes, retains all of the advantages of penetrometer emplacements.

Conventional cone penetrometer systems are already outfitted for soil gas and liquid sampling, geophysical measurements, in-situ chemical analysis, temperature logging, pore pressure measurements, and direction indicating capabilities. For example, permeability measurements are conducted with cone penetrometer emplacements by observing the dissipation of pore pressure after the soil has been compacted by the rod emplacement. The ability to obtain pore pressure data is included in a conventional geophysical measurement package located at the tip of the cone penetrometer. A disadvantage to this type of testing, however, is that this type of measurement requires a knowledge of the soil type to infer the soil's permeability, which in many cases is difficult to predict. Furthermore, this type of testing cannot be conducted in high permeability zones because the pressure dissipation in the soil is too rapid.

Conversely, conducting cone penetrometer testing using a spherical flow model, as described in the present invention, can provide detailed soil permeability data as a function of the depth at which the measurement is taken. This is because the testing region is relatively small (measured in fractions of a meter versus meters for the cylindrical model), allowing discrete measurements at high resolution in boreholes.

Therefore, it is an object of the present invention to provide a measurement method which allows quantitative in-situ determination of gas and saturated liquid permeability with a modified cone penetrometer and other direct push techniques.

It is also an object of the present invention to provide a soil permeability measurement method which substantially reduces field costs, is rapidly emplaced, generates minimal secondary waste generation and reduces worker exposure to chemical and radiological hazards.

It is a further object of this invention to obtain steady state measurements of air and saturated liquid permeability at various subsurface depths during a direct push technique which is unaffected by the compaction of the soil caused by the penetrometer.

It is also an object of the present invention to utilize a spherical flow geometry measurement method, in conjunction with direct push techniques, to obtain information relating to soil permeability as a function of depth.

It is another object of the present invention to provide a in situ measurement apparatus adapted to employ a spherical flow model to obtain information relating to soil permeability as a function of depth, without substantial disturbance of subsurface soil.

SUMMARY OF THE INVENTION

A method for discrete soil gas and saturated liquid permeability measurements with direct push emplacement systems (such as a cone penetrometer). A modified direct push emplacement system having at least one injection port and at least one monitoring port is first engaged to penetrate the soil to a predetermined depth. Gas or liquid is then injected into the soil at a predetermined location on the penetrometer rod. Next, a differential pressure response is recorded from at least two measurement ports, which are at a known distance from the injection port (on the same penetrometer rod). This pressure response data allows calculation of the soil permeability directly by using a one-dimensional, spherical, steady state, porous flow model to measure the effective permeability of the soil, without substantial disturbance of the surrounding soil.

The present invention is well-suited to direct push applications for a number of reasons. First, because the present method's environmental sphere of influence is small and discrete (e.g., in or around the direct push system), the amount of fluid injected into (or extracted from) the test region is small. This is important because of the limited space inside the direct push system for fluid pressure transfer lines and monitoring lines. Second, the present method does not require a long time period to reach a steady state condition. This provides for obtaining multiple measurements in relatively short periods of time while providing high spatial resolution. Third, the present invention's methodology is designed such that the compaction of soil adjacent to the rod, caused by the direct push system, has minimal impact on the inferred soil permeability.

DESCRIPTION OF THE INVENTION

Figure 1:
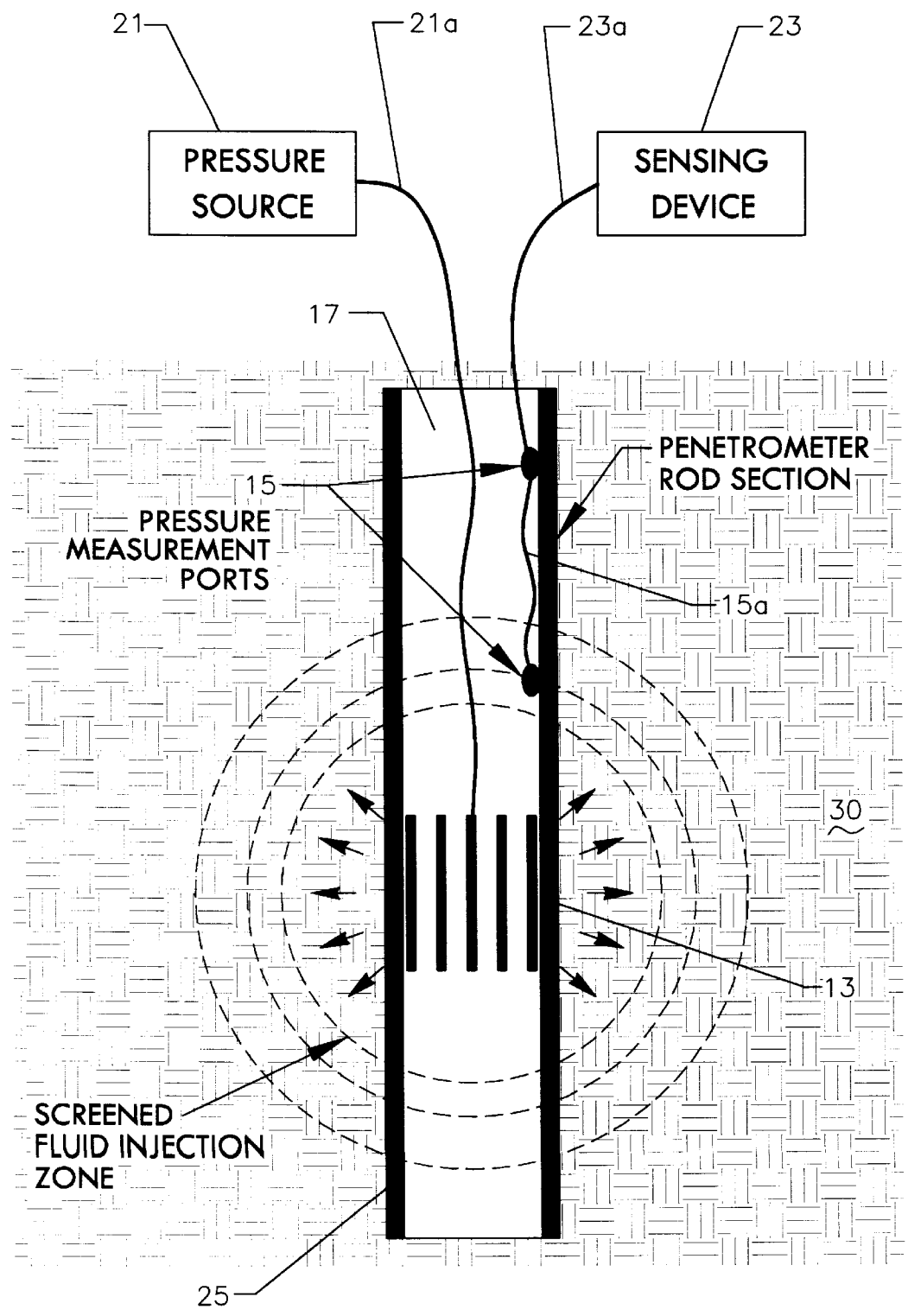
FIG. 1 is a partial cross sectional view of the present invention inserted into the subsurface.
Figure 3:
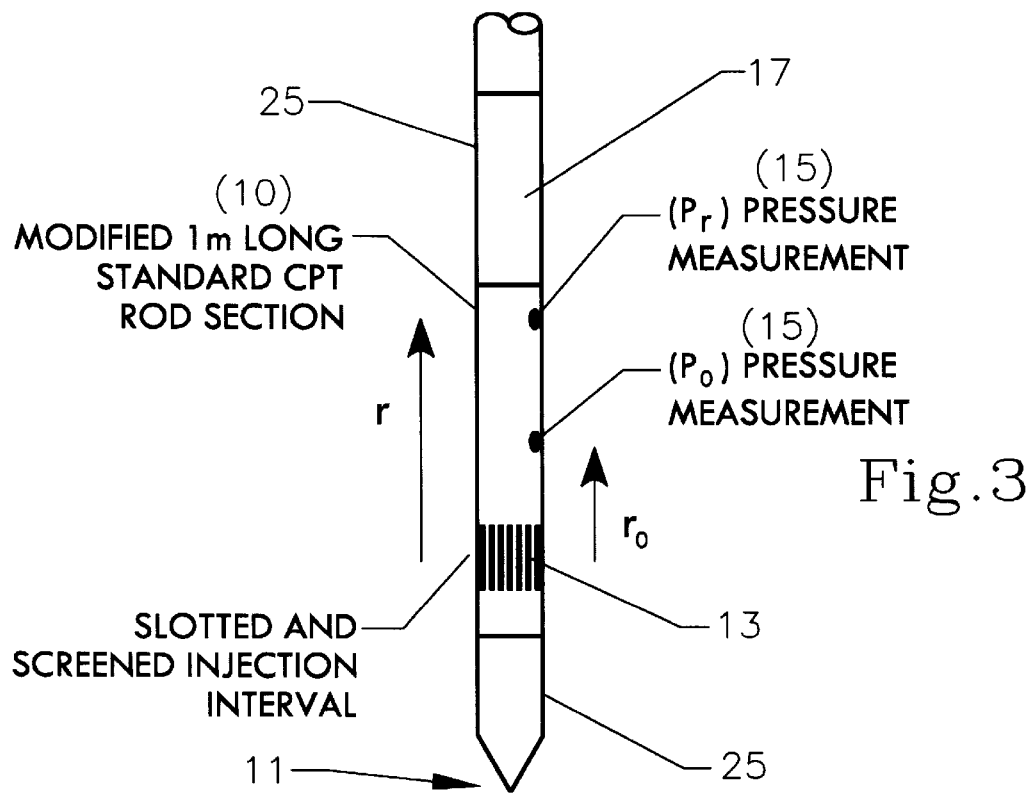
FIG. 3 is a partial cross sectional view of the present invention.

As seen in FIG. 1, the present invention includes a hollow-channeled penetrometer rod 10 having a cone 11 at one end (as seen in FIG. 3), at least one or more injection ports 13 and a plurality of measurement ports 15 along the length of rod 10, both ports integrally formed into or upon rod 10. In one embodiment, cone 11 on rod 10 is preferably of similar diameter as the diameter of rod 10. Each pressure port is in gas-flow communication with pressure sensor 23 through the hollow interior channel 17 of rod 10 and each port is formed at a predetermined radial distance away from any other port. In the preferred embodiment, each injection port 13 is at least equal to one half of the diameter of rod 10 to induce constant soil pressure in the adjacent environment.

Preferably, there is only a single injection port 13, and each injection port 13 is screened or slotted, is designed to allow air or fluid injection or extraction through the screened or slotted section, and is designed to assist the surrounding soil to reach equilibrium in a short time when subjected to fluid pressure. Further, measurement ports 15 would be fabricated at at least two locations above the extraction zone. These ports would be filtered penetrations into the probe which would allow pressure communication up to the ground surface. Thus, each injection port 13 is adapted to engage one end of a conventional injection line 21a through which either gas or liquid can flow. The exterior length of injection lines 21a is then placed within the interior channel 17 of rod 10, with the injection line's second end terminating at pressure source 21 above the surface to supply gas or liquid to injection port 13.

The plurality of measurement ports 15 are adapted to retain one or more sensor means 15a (as seen in FIG. 1) which are electrically or hydraulically connected via signal communication means 23a within the rod's interior channel 17 to one or more predetermined sensing devices 23 located above the surface. Such sensing devices, for example, can include a wire, a conventional manometer, or a computer, all adapted to electrically communicate with the sensor means and being capable of receiving soil permeability measurement data.

Figure 2:
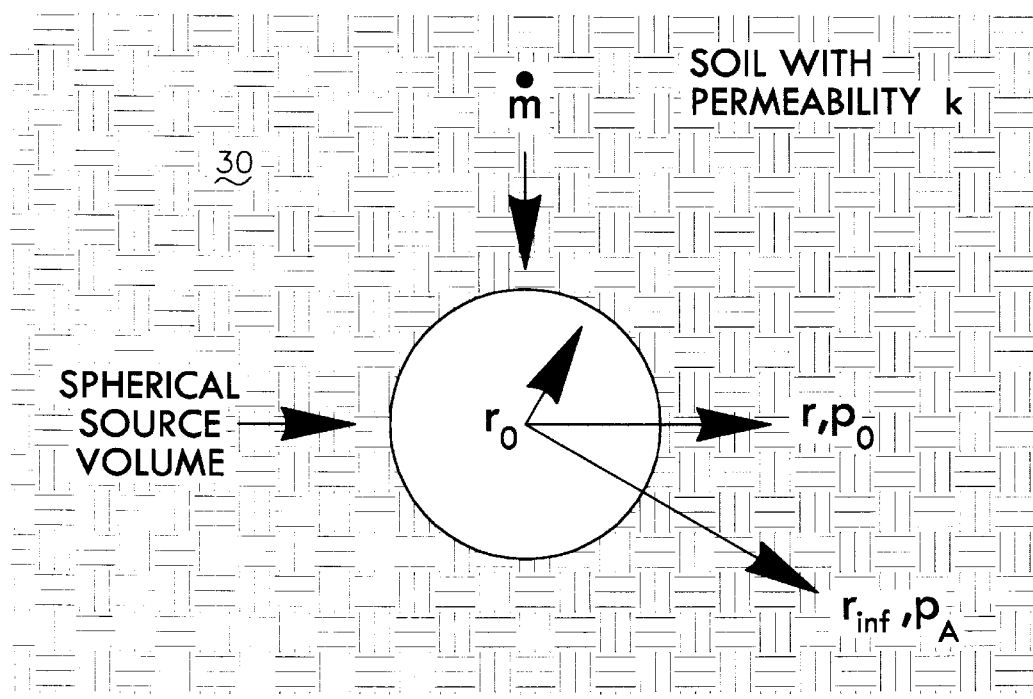
FIG. 2 is a graphical representation of the fluid flow field when the present invention is employed.

To obtain soil permeability measurements, rod 10 is inserted (or, pushed) into the ground by any conventional means. The interior channel 17 of rod 10 will contain the necessary injection lines and electrical signal wires which connect to the injection ports and measurement ports, respectively. As rod 10 is inserted into the subsurface, and because cone 11 is of substantially similar diameter as the diameter of rod 10, the rod's 10 exterior surface 25 will have a tight fit above and below the injection ports and measurement ports. Then, a fluid, such as a liquid or a gas, is injected through injection line 21a (or extracted from the injection line) to an injection port 13 on the penetrometer rod 10. This injection (or extraction) will result in a spherical flow field as the fluid moves outward from the rod, and is required to induce an equilibrium in the surrounding soil for accuracy. In most circumstances, soil equilibrium is achieved in less than five minutes. Subsequently, the flow field will become essentially spherical even if the soil adjacent to the rod is of a much lower permeability (due to soil compaction). As represented in FIG. 2, the injection or extraction source is represented as a spherical volume with radius $r_o$. Fluid is added (or removed) from the zone at a known rate. The medium has a permeability, k, which is assumed homogeneous.

Eventually, equilibrium will be reached, which means that for any given injection rate, the radial pressure profile along the axis of penetrometer rod 10 is identical to that which would occur if rod 10 (and compacted soil) did not exist. Once equilibrium has been reached, a permeability measurement is obtained from the sensing means 23a and communicated to sensing devices 23. Measurement of the pressure gradient at some distance from the injection port produces adequate information to infer the permeability accurately. Subsequently, rod 10 can be further pushed into the subsurface 30 for additional or repetitive testing. In light of the foregoing, those of skill in the art will realize that additional measurements can be obtained through sensing means 23a, such as atmospheric pressure, temperature, and fluid flow rate.

When the exterior surface of rod 10 is in tight fitting relationship with the immediate soil, the permeability test data results may be heavily influenced by the compacted soil annulus formed as penetrometer 10 is forced into the adjacent soil. A compacted layer as thin as half a centimeter would likely result in artificially low inferred permeability due to the high pressure gradient caused in this region by the reduction of soil porosity. As such, the pressure field will eventually become spherical as the distance from the injection zone increases. The details of the extraction source geometry can be ignored if radial pressure measurements are taken at a distance from the source. The resulting radial pressure profile then allows the definition of $r_o$ as the distance from the extraction source to the first pressure measurement location (as seen in FIG. 2).

Figure 4:
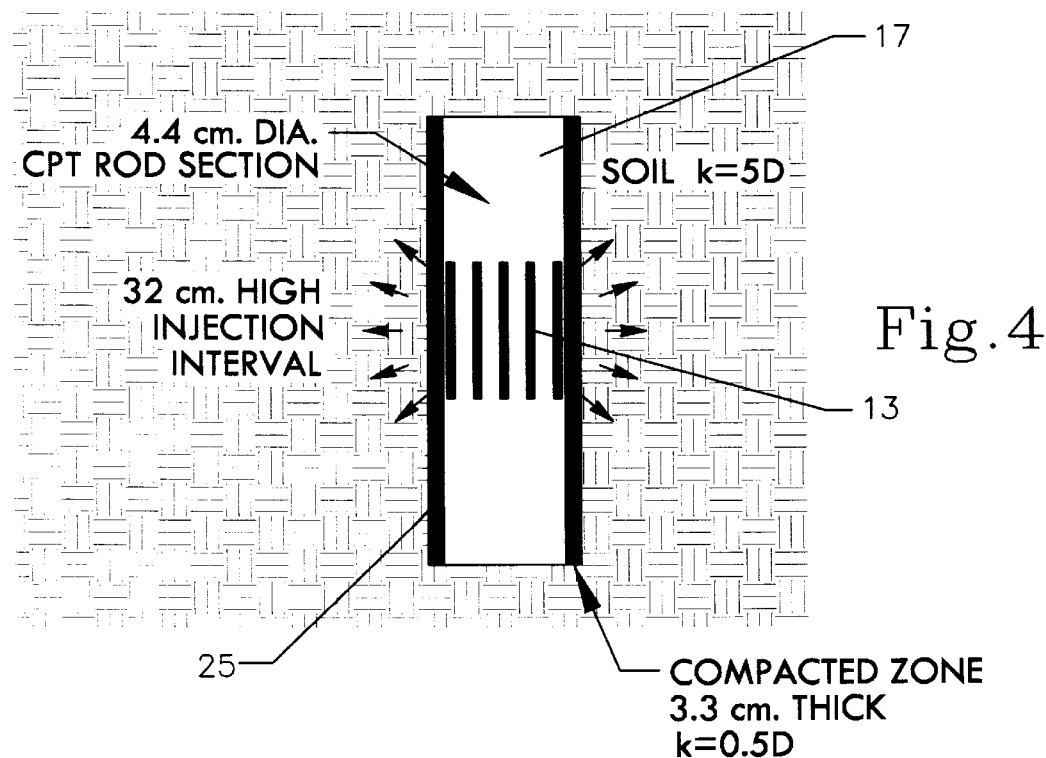
FIG. 4 is a partial cross sectional view of the present invention as tested in the laboratory.
Figure 5:
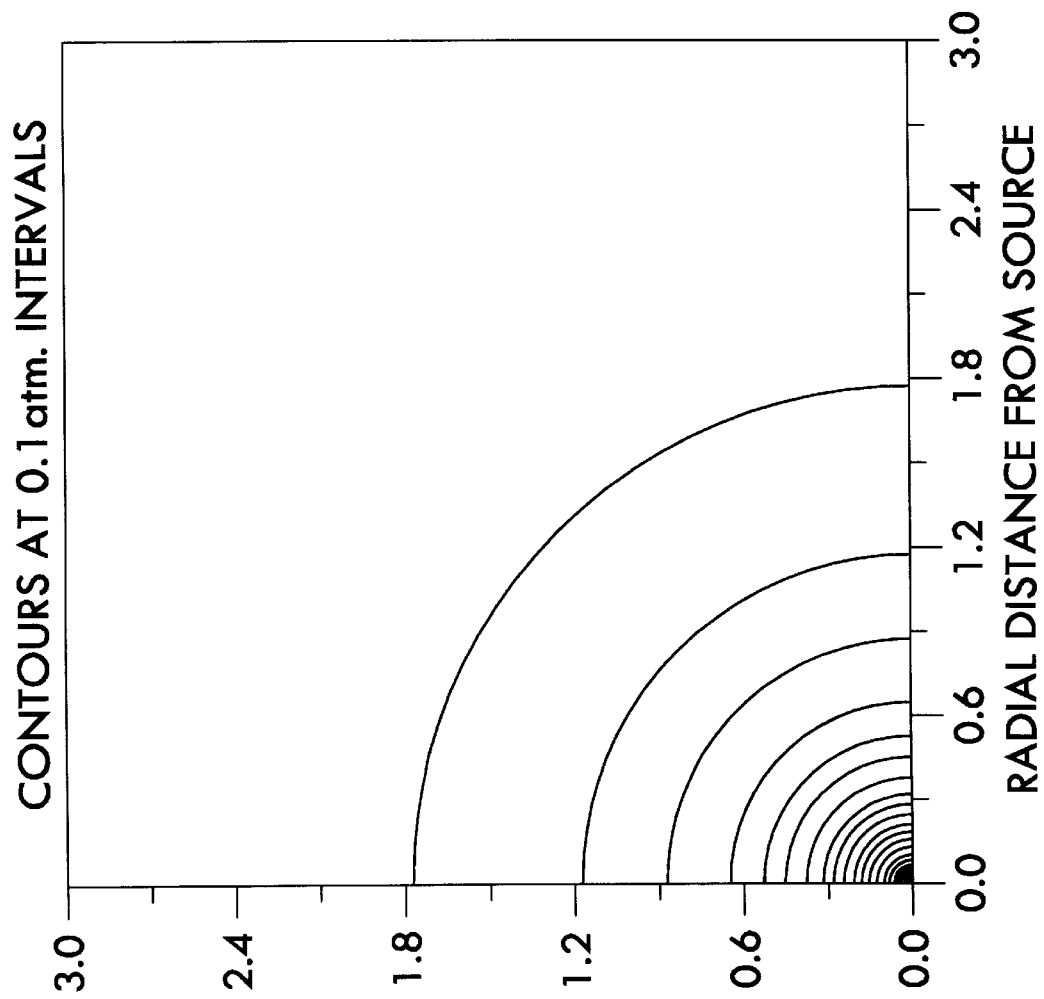
FIG. 5 is a graphical illustration of the gas pressure distribution adjacent to the test set up according to FIG. 4.
Figure 6:
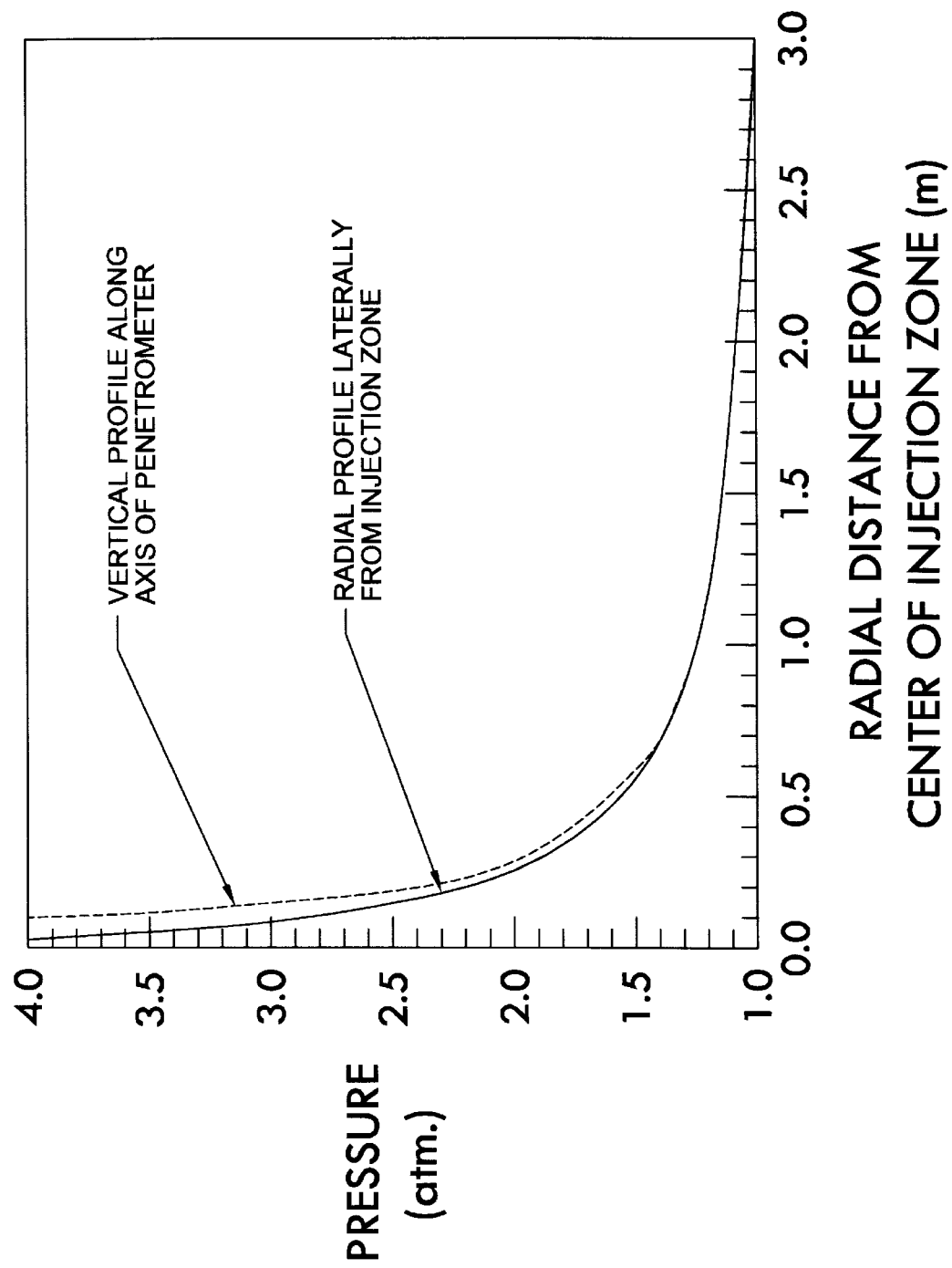
FIG. 6 is a graphical illustration of the pressure profiles along and perpendicular to the axis of a penetrometer rod as set up according to the configuration of FIG. 4.
Figure 12:
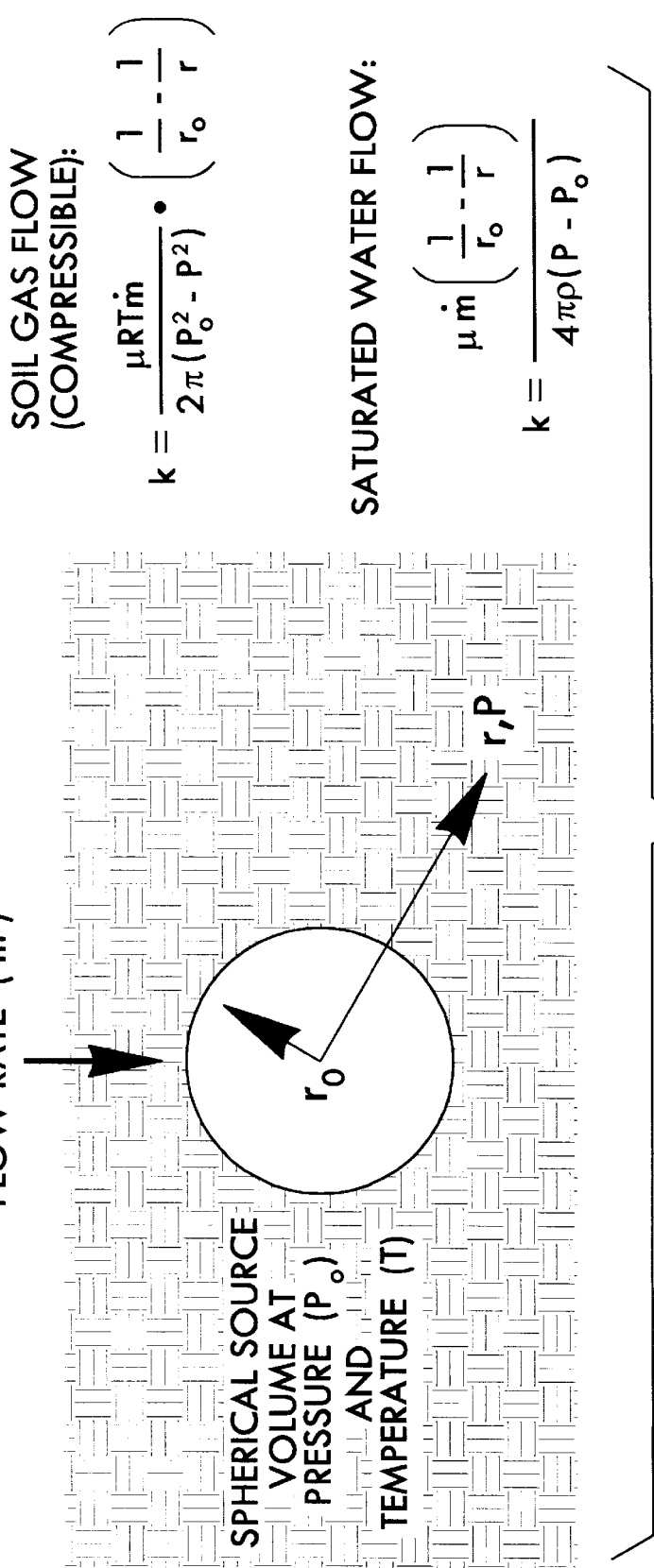
FIG. 12 illustrates the one dimensional steady state, spherical porous flow model disclosed in the present invention.

FIGS. 4 and 6 exemplify a laboratory test simulation where the steady state radial symmetric AIRFLOW code was used to model the soil gas response. In this example, a 4.4 cm-diameter penetrometer with a 32 cm-high screened injection zone is emplaced in soil with a uniform permeability of 5 Darcies. The resulting contour plot (as seen in FIG. 5) indicates that at a short distance from the injection source, the isobars become very spherical. The cylindrical geometry eventually results in a spherical flow field. At slightly less than 0.5 of a meter from the injection source, the pressure profile along the axis of the penetrometer equals the profile radially outward from the penetrometer rod. Additionally, as seen in FIG. 12, a one dimensional steady state flow model is employed to generate the desired information. In particular, R is the universal gas constant, $P_o$ is the pressure inside the sphere, P is the pressure outside of the sphere, $r_o$ is the radius within the sphere, r is the radius outside of the sphere, ρ is the density, μ is the viscosity of the injection fluid, T is the temperature, and m is the fluid's flow rate. Those of skill in the art will realize that with obtaining the proper data, this model can be employed in a data acquisition unit and analysis device without undue experimentation to obtain the desired results.

Figure 7:
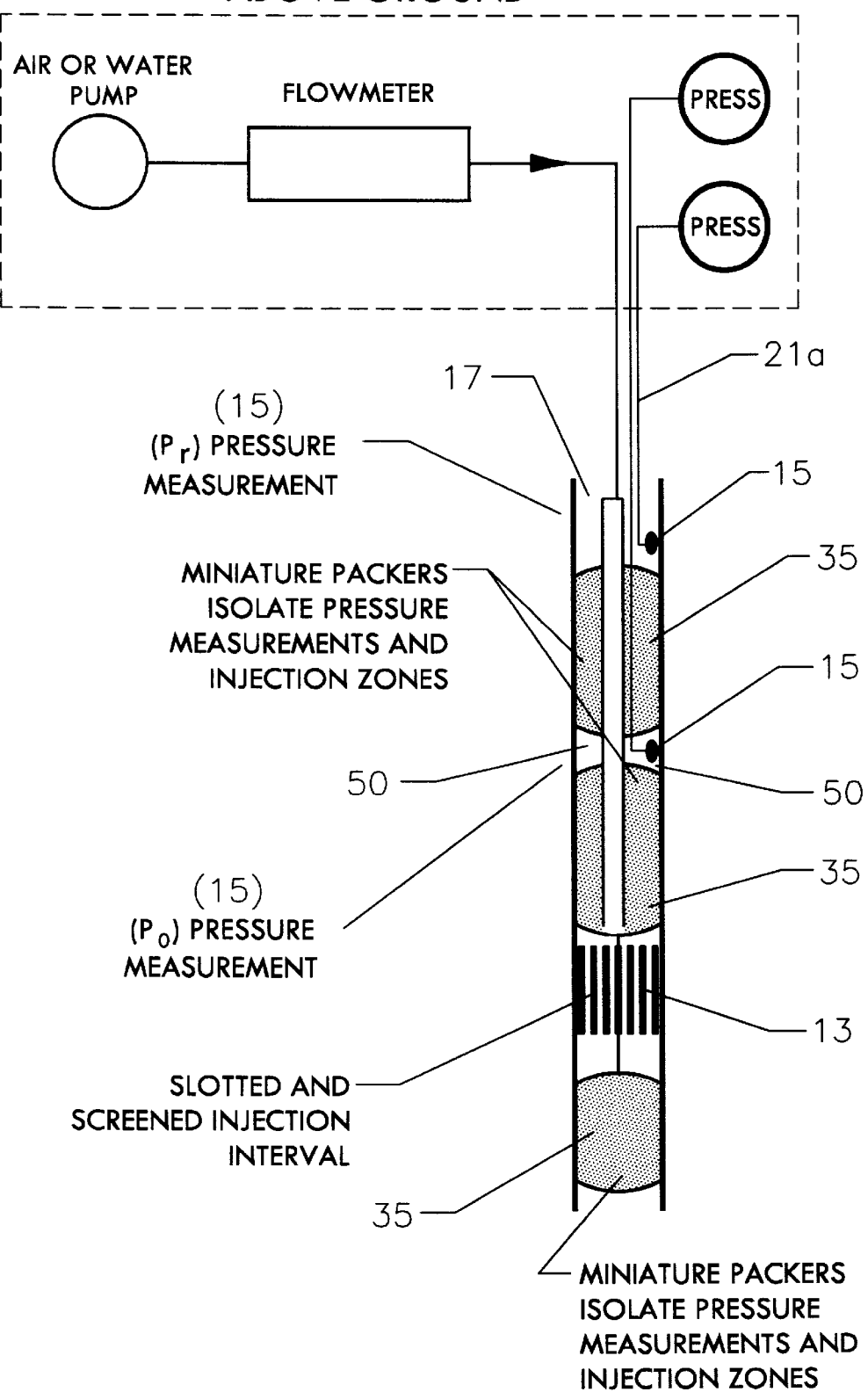
FIG. 7 is an alternate embodiment of the present invention.
Figure 9:
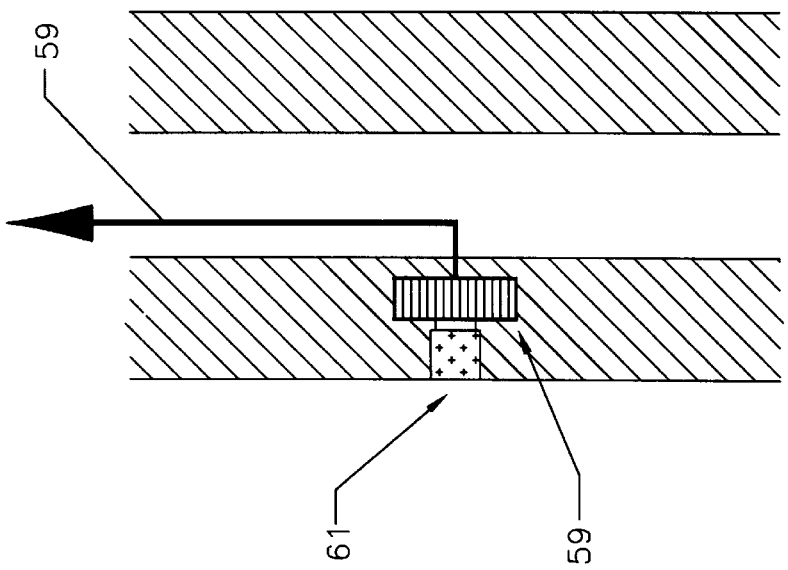
FIG. 9 is a detailed view of a portion of the embodiment shown in FIG. 8.
Figure 8:
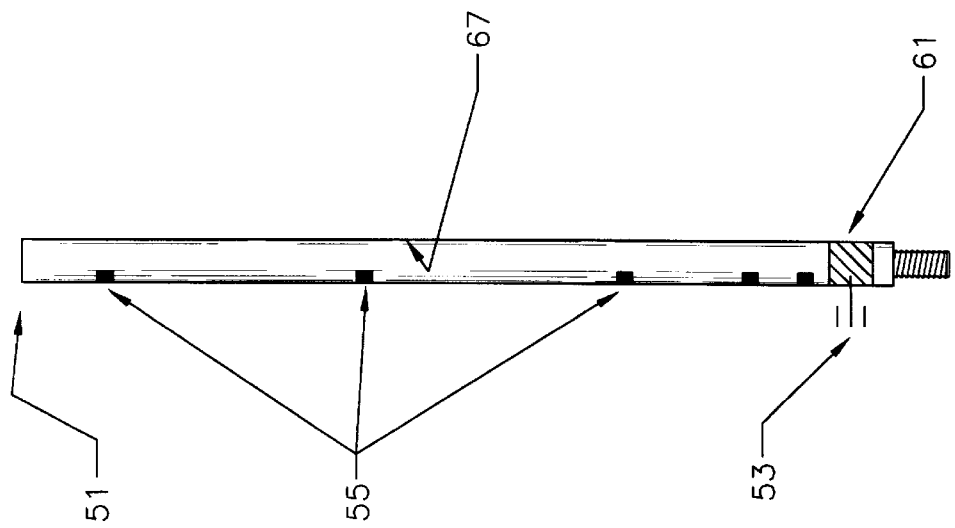
FIG. 8 is a side view of an alternate embodiment of the present invention.

In geographic areas composed of highly saturated conditions, an alternative embodiment of the present invention is adapted to obtain permeability measurements using inflatable packers inside of the rod. In this fashion, and as seen in FIG. 7, miniature packers 35 are secured along the penetrometer rod at preselected intervals. Each packer 35 is capable of being inflated, so that when rod 10 is at the desired subsurface depth, all the packers are inflated to provide a stable support structure for the rod and also provide a plurality of enclosed testing regions 50. Each testing region 50 includes a port 15 which allows fluid pressure communication with the soil. The packer 35 allows injection of air into the soil while the pressure measurements accurately monitor soil gas pressure. This design has the advantage of leaving the penetrometer rod open for other uses. In operation, each testing region 50 can either be an injection port 13 or a measurement port 15.

An alternate embodiment of the present invention is shown in FIGS. 8–11. In this embodiment, a direct push emplacement system is mounted on a truck for portability. The system includes rod 51 similar to rod 10 above, and preferably, is a conventional two inch diameter by approximately three foot long length. The internal channel of rod 51 includes tubing 67 which can transport fluid from the earthen surface to the point of desired injection (defined as the injection zone). Gas (such as air) or liquid (such as water) is injected into the soil through a screened or filtered portion 53 located at the bottom of rod 51. Rod 51 includes a plurality of precision pressure sensors 55 (preferably five) embedded in rod 51 to measure the pore fluid pressure in the soil at specific distances from the injection zone. The electrical signals generated from sensors 55 are then transmitted to the earthen surface to a data acquisition unit 57 (such as a computer) by conventional means, such as electrical wire or cable 59. The fluid injection zone pressure and temperature inside rod 51 are measured with sensors 61. Like sensors 55, the information generated by sensors 61 is transmitted to the earthen surface through conventional means, such as cable 59.

Figure 11:
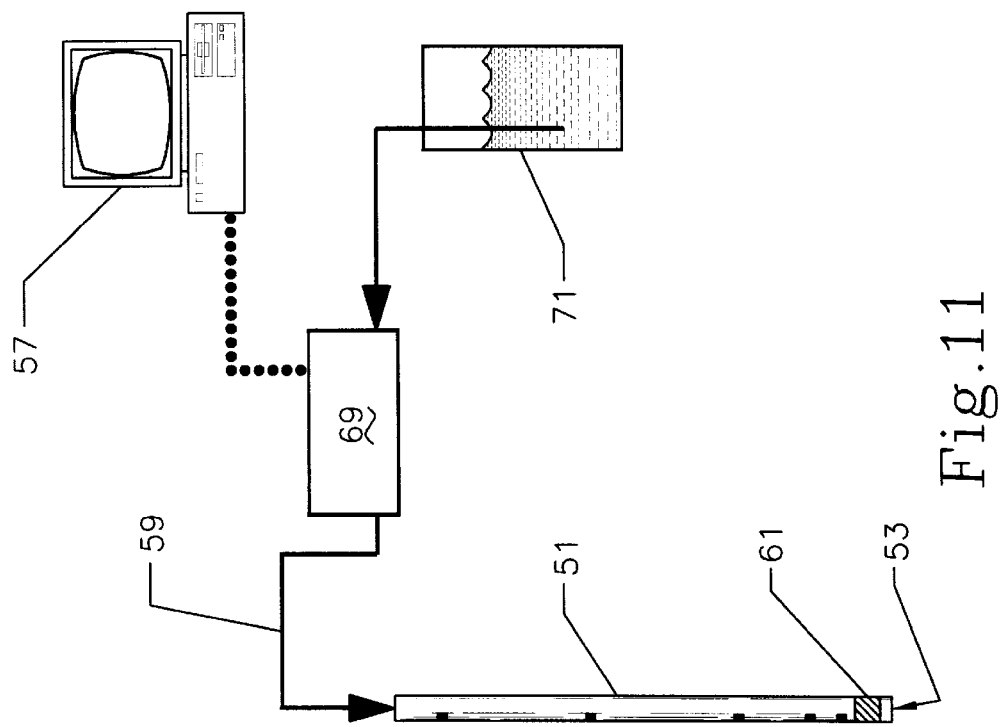
FIG. 11 is another side view of the invention illustrated in FIG. 8, depicting additional components disclosed.
Figure 10:
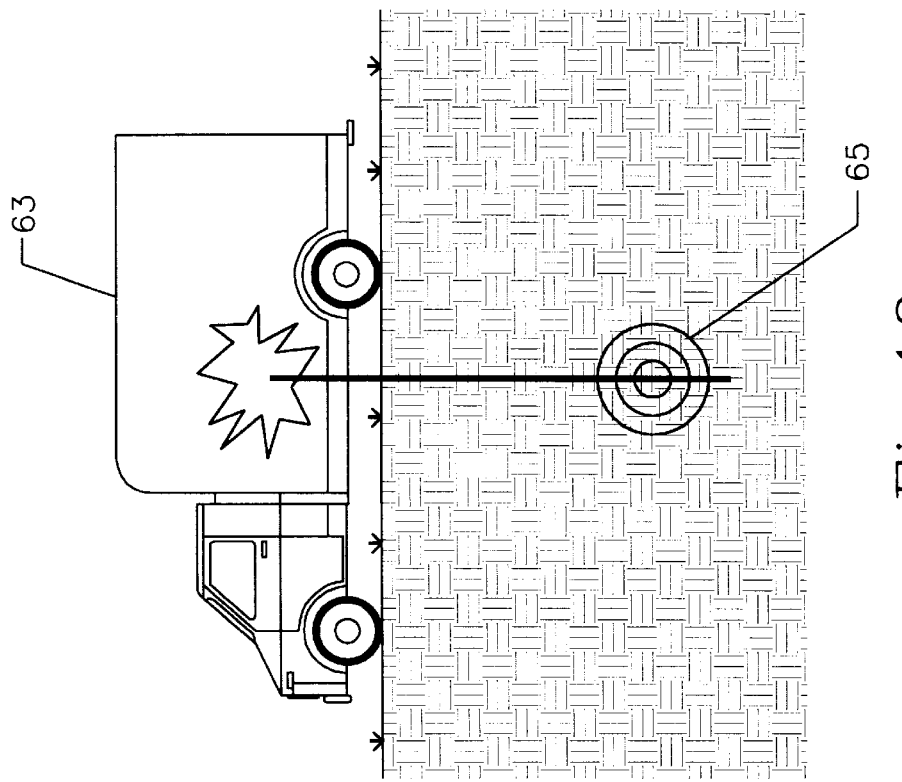
FIG. 10 graphically illustrates the portable vehicle employed with the invention of FIG. 8.

As seen in FIGS. 10–11, the alternate embodiment is employed by stationing truck 63 over a preselected measurement location 65. Penetrometer rod is pushed to the desired measurement depth 65. Gas or fluid is then pumped into the injection tubing 67 from box 69 containing the gas and fluid pumps. For example, a reservoir of clean water 71 (or similar fluid) can be used to provide the injection fluid. Preferably, pump box 69 also includes meters (not shown) that measure the gas and fluid flow rates. Signals from these flow meters, and pressure sensors 55, 61 in the rod section, can then be transmitted to data acquisition unit and analysis device 57 through cable 59. Data acquisition unit and analysis device 57 calculates the permeability using mathematical models described above. The advantage of the present invention is that it provides higher quality data and will work over long distances (e.g., hundreds of feet). In contrast, the previous methods are difficult to employ using long pressure measurement tubes.

The present invention offers several advantages over conventional soil permeability techniques. For example, the present invention provides an absolute measure of soil permeability and is adapted to measure a wide range of soil permeability conditions in both saturated and unsaturated soil. The invention also does not require permanently occupying the inner core of the penetrometer and is designed to pass other electrical signals and tubes running to measurements at the penetrometer's tip. Finally, the cost savings of this method, when compared to drilled borehole measurements, are significant. Borehole formation costs range from tens to hundreds of thousands of dollars for a typical well, depending on the type of drilling operation, nature of contamination, depth of well, and the geologic media. Additionally, a typical drilling operation for a 100 ft. well requires two to five days. In contrast, the method of the present invention can be accomplished in one day with a full suite of measurements. In both gas and liquid permeability measurements, the measurement time per station is less than five minutes, so 20 to 40 measurements could be accomplished during one push, in one day. This provides a great deal of detail in permeability distribution.

Whereas the drawings and accompanying description have shown and described the preferred embodiment of the present invention, it should be apparent to those skilled in the art that various changes may be made in the form of the invention without affecting the scope thereof.

We claim:

1. An apparatus for determining soil permeability at a particular extraction zone, the apparatus comprising:
   (a) an elongated penetrometer rod of predetermined diameter having an internal channel formed therein;
   (b) a cone attached on one end of the rod;
   (c) a plurality of measurement ports formed at specific locations upon the rod, each measurement port being filtered and in gas-flow communication with the channel;
   (d) a plurality of injection ports formed upon the rod in gas-flow communication with the channel;
   (e) a means, partially located within the rod's channel, for communicating pressure information, each means for communicating pressure information having a first end and a second end, each means for communicating pressure information being attached to each measurement port at each first end; and
   (f) a means for sensing pressure information attached to the means for communicating pressure information at the means for communicating pressure information's second end, the means for sensing pressure information being remotely located from the rod, the means for sensing pressure information adapted to employ a one dimensional steady state spherical porous flow model to obtain a desired result.

2. The apparatus of claim 1, further including a means, partially located within the rod's channel, for injecting fluid flow having a primary end and a secondary end, each means for injecting fluid flow being attached to each injection port at each primary end.

3. The apparatus of claim 2, further including means for inducing pressure attached to the means for injecting fluid flow at the secondary end, the means for inducing pressure remotely located from the rod.

4. The apparatus of claim 3, wherein the means for injecting fluid flow is adapted to allow the flow of gas.

5. The apparatus of claim 3, wherein the means for injecting fluid flow is adapted to allow the flow of liquid.

6. The apparatus of claim 3, wherein the means for injecting fluid flow is an injection line.

7. The apparatus of claim 3, wherein each injection port is at least equal in width to one half of the rod's diameter.

8. The apparatus of claim 7, wherein each injection port further includes a screen attached thereto and is adapted to allow fluid injection or extraction through the screen, thereby assisting the surrounding soil to reach equilibrium when subjected to fluid pressure.

9. The apparatus of claim 3, wherein each injection port is wider than the width of each measurement port's predefined diameter.

10. The apparatus of claim 9, wherein the cone is of predefined diameter and equal to the diameter of the rod.

11. The apparatus of claim 2, further including one or more sensor means displaced within each measurement port, the means for communicating pressure information being in electrical communication with each sensor means at the first end, each sensor means adapted to receive soil permeability measurement information.

12. The apparatus of claim 11, wherein each sensor means is selected from the group of a wire, a manometer, an electronic pressure sensor, or a computer.

13. The apparatus of claim 11, wherein only two measurement ports are formed upon the rod at a distance above the extraction zone.

14. A device for discrete soil gas and saturated liquid permeability measurements at a particular extraction zone with direct push emplacement systems, the device comprising a hollow channeled direct push emplacement system having at least two measurement ports and at least one injection port formed upon the system, the injection port being filtered and in gas-flow communication with the channel; the device further comprising a means, partially located within the channeled direct push emplacement system, for communicating pressure information, each means for communicating pressure information having a first end and a second end, each means for communicating pressure information being attached to each measurement port at each first end; and a means for sensing pressure information attached to the means for communicating pressure information at the means for communicating pressure information's second end, the means for sensing pressure information being remotely located from the rod, the means for sensing pressure information employing a one dimensional steady state spherical porous flow model to obtain a desired result.

15. The device of claim 14, wherein the system is an elongated penetrometer rod of predetermined diameter, the system further including a cone attached on one end of the rod.

16. The device of claim 15, further including a means for injecting fluid partially located in the system's hollow channel and having a primary end and a secondary end, the means for injecting fluid being coupled to each injection port, and a means for inducing pressure, the means for inducing pressure being coupled to the means for injecting fluid at the secondary end.

17. The device of claim 16, wherein the means for injecting fluid is adapted to allow the flow of gas or liquid.

18. The device of claim 16, further including a sensor means displaced within each measurement port; a means for communicating pressure information partially located in the system's hollow channel and having a first end and a second end, the means for communicating pressure information being electrically coupled to each sensor means at each first end; and a means for sensing pressure information coupled to each means for communicating pressure information's second end.

19. The device of claim 18, wherein each injection port is at least equal to one half of a diameter of the system and wider than a width of each measurement port, each injection port further including a filter attached thereto and adapted to allow fluid injection or extraction through the filter to assist the surrounding soil to reach equilibrium when subjected to fluid pressure.

20. A method for discrete soil gas and saturated liquid permeability measurements at a particular extraction zone within the earth with direct push emplacement systems, the method comprising the steps of:

(a) inserting a direct push emplacement system into the earthen soil to a predetermined depth, the system having a hollow channel and at least two measurement ports and at least one injection port formed upon and within the system, each measurement port and each injection port being filtered and in communication with the channel, each measurement port being of predetermined radial distance away from any injection port; the system further including a means for injecting fluid and a means for inducing pressure, the means for injecting fluid being partially located in the system's hollow channel and having a primary end and a secondary end, the means for injecting fluid being coupled to each injection port at each primary end, the means for inducing pressure being coupled to the means for injecting fluid at each secondary end; the system further comprising sensor means and a means for communicating pressure information and a means for sensing pressure information, the sensor means residing within each measurement port; the means for communicating pressure information partially located in the system's hollow channel and having a first end and a second end, the means for communicating pressure information being electrically coupled to each sensor means at each first end, the means for sensing pressure information coupled to each means for communicating pressure information's second end;

(b) allowing the means for inducing pressure to dispense or extract fluid to or from the means for injecting fluid and thereafter to each injection port formed within the system to result in a spherical flow field which subsequently provides an equilibrium in the surrounding earthen soil;

(c) obtaining permeability measurement information from each sensing means;

(d) transmitting the permeability measurement information to the means for sensing pressure information through the means for communicating pressure information; and (e) employing a one dimensional steady state spherical porous flow model within the means for sensing pressure information to obtain a desired result.

21. The method of claim 20, wherein the system is an penetrometer rod of predetermined diameter, the rod further having a cone attached thereto.

22. The method of claim 21, further including the steps of obtaining atmospheric pressure information, soil temperature information and fluid flow rate information from each sensing means.

23. The method of claim 22, further including the step of employing inflatable packers within the rod at preselected intervals to define one or more testing regions along the length of the rod adjacent to each measurement port or each injection port.

24. An instrument for soil gas, fluid and permeability measurements at desired locations below the earthen surface, the instrument comprising:

(a) an elongated, channeled direct push emplacement system having a tube therein and a top end and a bottom end, the system further including at least one filter located adjacent to the bottom end;

(b) a plurality of pressure sensors variously embedded along the length of the system and adapted to measure soil pore pressure at various positions from the desired locations, each pressure sensor being adjacent to a filter;

(c) means for communicating pressure information partially located within the tube and having a first, a second, a third, and a fourth end, the first end being in electrical communication with each pressure sensor and each pore pressure sensor;

(d) means for pumping gas or fluid, the means for pumping gas or fluid being coupled with the means for communicating pressure information's second and third ends; and (e) at least one data acquisition and analysis means being in electrical communication with the means for communicating pressure information's fourth end.

25. The instrument of claim 24, wherein the means for pumping gas or fluid further comprises a plurality of meters for measuring gas and fluid flow rates, each meter being in electrical connection with each data acquisition and analysis means.

26. The instrument of claim 25, further including a fluid reservoir attached and in fluid communication with the means for pumping gas or fluid.

27. The instrument of claim 25, further including a transportation vehicle, the emplacement system being carried and supported by the vehicle.

28. The instrument of claim 27, wherein the direct push emplacement system is an elongated penetrometer rod.

* * * * *